United States Patent [19]

Ahr et al.

[11] Patent Number: 4,909,802
[45] Date of Patent: Mar. 20, 1990

[54] ABSORBENT GARMENT HAVING A WAIST BELT ATTACHMENT SYSTEM

[75] Inventors: Nicholas A. Ahr, Cincinnati; William G. Pierce, Mason, both of Ohio

[73] Assignee: The Procter & Gamble Company, Cincinnati, Ohio

[21] Appl. No.: 39,552

[22] Filed: Apr. 16, 1987

[51] Int. Cl.[4] .................................. A61F 13/16
[52] U.S. Cl. .................................. 604/385.1; 604/392
[58] Field of Search ............... 604/385.1, 392, 397, 604/398

[56] References Cited

U.S. PATENT DOCUMENTS

| | | | |
|---|---|---|---|
| 849,725 | 4/1907 | Cook | 604/398 |
| 2,011,027 | 8/1935 | Ballard et al. | 604/398 |
| 2,224,518 | 12/1940 | Lakritz | 128/284 |
| 3,110,312 | 11/1963 | Wirth | 128/287 |
| 3,146,464 | 9/1964 | Burnett | 2/49 |
| 3,386,442 | 6/1968 | Sabee | 128/287 |
| 3,407,813 | 10/1968 | Grippo et al. | 604/398 |
| 3,618,608 | 11/1971 | Brink | 128/287 |
| 3,771,524 | 11/1973 | Ralph | 604/398 |
| 3,793,644 | 2/1974 | Kellner | 2/49 R |
| 3,851,760 | 12/1974 | Smith | 2/49 R |
| 3,890,973 | 6/1975 | Davis et al. | 604/392 |
| 4,051,854 | 10/1977 | Aaron | 128/284 |
| 4,315,508 | 2/1982 | Bolick | 128/289 |
| 4,555,244 | 11/1985 | Buell | 604/392 |
| 4,560,380 | 12/1985 | Tharel | 604/385.1 |
| 4,578,671 | 3/1986 | Buell | 604/385.1 |
| 4,601,717 | 7/1986 | Blevins | 604/385.1 |
| 4,617,022 | 10/1986 | Pigneul et al | 604/394 |
| 4,728,326 | 3/1988 | Gilles | 604/385.1 |
| 4,771,483 | 9/1988 | Hooreman et al. | 604/392 |

FOREIGN PATENT DOCUMENTS

| | | | |
|---|---|---|---|
| 1064444 | 9/1959 | Fed. Rep. of Germany | 604/385.1 |
| 0988191 | 8/1951 | France | 604/385.1 |
| 2566631 | 1/1986 | France | 604/358 |
| 2586558 | 3/1987 | France . | |
| 0914129 | 12/1962 | United Kingdom | 604/385.1 |

OTHER PUBLICATIONS

Webster Dictionary, 1984.

Primary Examiner—C. Fred Rosenbaum
Assistant Examiner—Mark O. Polutta
Attorney, Agent, or Firm—Larry L. Huston; John M. Pollaro; Fredrick H. Braun

[57] ABSTRACT

An integral disposable absorbent garment, such as a disposable diaper or incontinent brief, having an integral belt segment on each side of the garment. The integral belt segments, in association with a receiving or attachment means, are intended to hold or suspend the garment about the lower torso of the wearer.

11 Claims, 5 Drawing Sheets

ABSORBENT GARMENT HAVING A WAIST BELT ATTACHMENT SYSTEM

FIELD OF THE INVENTION

The present invention relates to integral disposable absorbent garments such as disposable diapers, and in particular to disposable diapers having a single integral belt segment in each side margin of the garment for use as part of a waist belt attachment system.

BACKGROUND OF THE INVENTION

Garments of the general type described are well-known. In particular, disposable diapers and incontinent garments are widely described in the patent literature and elsewhere. Among such publications are patents that relate to classes of garments that are provided with various suspension or attaching means. For example, U.S. Pat. No. 4,315,508, which issued to M. E. Bolick on Feb. 16, 1982, teaches a waist suspension system comprising a non-integral, fully detachable elastic strip on each side of the garment, the ends of the strips being provided with buttons or other fastening means intended to cooperate with means provided in the diaper material such as buttonholes. Essentially, the elastic strips act like suspenders on the wearer's hips and hold the diaper in place. U.S. Pat. No. 3,386,442, which issued to R. Sabee on June 4, 1968, teaches a disposable diaper of a generally rectangular shape in which the diaper material in each side margin is longitudinally cut or perforated from just inside one end of the diaper to just inside the other. A lateral perforation is also made along the diaper's lateral axis extending from the longitudinal perforation to the outside edge of the diaper. When ready for use, the perforations are broken, resulting in two integral belt segments being formed in each side margin of the diaper to be knotted or otherwise held together about the waist of the wearer. Lastly, U.S. Pat. No. 2,224,518, which issued to J. H. Lakritz on Dec. 10, 1940, teaches a nondisposable diaper of generally rectangular shape having integral ties (belt segments) which are formed as forwardly extending continuations of the side margins of the diaper. The ties are adapted to be insertable through openings at the opposite end of the diaper so as to fasten the diaper about the wearer.

Garments of the type described in the prior art, as well as those which have been available commercially, suffer from one or more of the following deficiencies: they are uncomfortable in that the elastic strips and buttons tend to irritate the wearer; they are size-dependent and unable to accommodate a variety of wearers; they tend to sag in use resulting in significant leakage; they are expensive to manufacture; and they are not readily refastenable, thereby inhibiting a parent, an incontinent, or a person in charge of a incontinent from opening the garment and examining for wetness or from easily lowering and then refastening the garment when using bathroom facilities.

Therefore, it is an object of the present invention to provide a combination of an absorbent garment and a waist belt attachment system which overcomes, to a great degree, the deficiencies in the prior art structures. It is an additional object of the present invention to provide an absorbent garment having a single integral belt segment in each side margin of the garment for use as part of a waist belt attachment system.

While the subject technology has application on all diaper-like garments, it has particular application on diaper-like garments in which the sides of the garment do not meet along the sides of the wearer when worn, as is often the case with adult size garments.

SUMMARY OF THE INVENTION

In accordance with the present invention, an integral disposable absorbent garment, such as a diaper, is provided with a chassis means and a waist belt attachment system joined to the chassis means. The chassis means comprises an absorbent core having a garment surface, a body surface, and side edges; a liquid impervious backsheet positioned adjacent the garment surface of the absorbent core; and a liquid pervious topsheet positioned adjacent the body surface of the absorbent core. The waist belt attachment system comprises two integral belt segments and a receiving means for use in association with the integral belt segments. The integral belt segments and the receiving means are joined to the chassis means and are intended to cooperate with each other to hold or suspend the diaper about the lower torso of the wearer.

The backsheet and/or topsheet of the garment have dimensions such that they extend beyond the side edges of the absorbent core into side margins. Preferably, the integral waist belt segments are formed in each side margin of the garment by longitudinally cutting or perforating a certain length of the backsheet and/or topsheet material in each side margin and ending the cut before exiting the back end of the garment. Thus, each integral belt segment has a fixed point which is permanently affixed to the chassis means and a distal point which is free, or which can easily be made free, from the chassis means. Receiving means, such as double-faced adhesive tapes are placed on the garment surface of the backsheet near the front waist portion of the garment so as to interact with the distal points of the integral belt segments during use. The integral belt segments, in association with the receiving means, hold or suspend the chassis means about the lower torso of the wearer.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements and in which:

DETAILED DESCRIPTION OF THE PREFERRED EMBODIMENTS

The present invention relates to integral disposable absorbent garments such as disposable diapers, and more particularly, to integral disposable absorbent garments having an improved waist belt attachment system.

Figure 1:
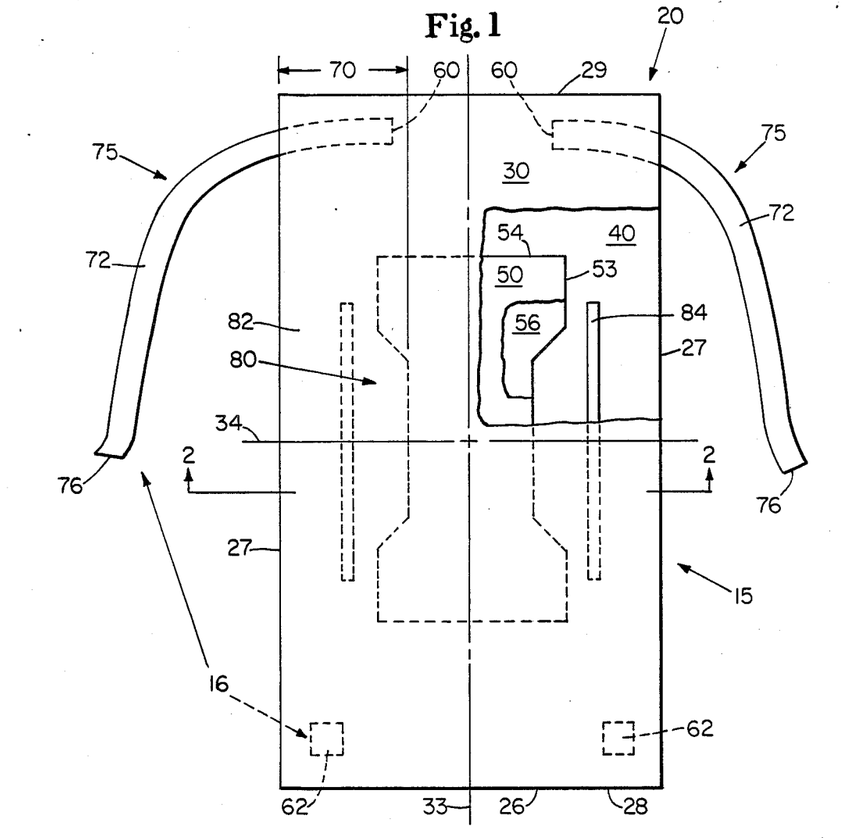
FIG. 1 is a plan view of a disposable diaper embodiment of the present invention having portions cut away to reveal underlying structure and with the portion of the diaper which contacts the wearer facing the viewer.

As used herein, the term "integral disposable absorbent garment" refers to articles which absorb and contain body exudates and more specifically refers to articles which are placed against or in proximity to the body of a wearer to absorb and contain the various exudates discharged from the body and which are intended to be discarded after a single use (i.e., they are not intended to be laundered or otherwise restored or reused), and which are unitary in that they do not require separate manipulative parts like a separate holder and liner. A preferred embodiment of the integral disposable absorbent garment of the present invention is shown in FIG. 1 as it would be used in a diaper 20. As used herein, the term "diaper" refers to a garment generally worn by infants or other incontinent persons about the lower torso.

FIG. 1 is a partially cut away plan view of the diaper 20 of the present invention in its flat out, uncontracted state (i.e., with all elastic induced contraction pulled out) with portions of the structure being cut-away to more clearly show the construction of the diaper 20 and with the portion of the diaper 20 which contacts the wearer facing the viewer. As can be seen in FIG. 1, the diaper 20 basically comprises a chassis means 15 and a waist belt attachment system 16. The waist belt attachment system 16 further comprises two integral belt segments 72 and a receiving means 62 for use in association with the integral belt segments 72. The chassis means 15 may be any means which is generally compressible, conformable, non-irritating to the wearer's skin, and capable of absorbing and containing body exudates, such as feces, urine, blood, pus, and the like. The chassis means 15 has chassis side edges 27 and chassis front and chassis back end edges 28 and 29, respectively. In the preferred embodiment shown in FIG. 1, the chassis means 15 comprises a liquid pervious topsheet 30; a liquid impervious backsheet 40; and an absorbent core 50 positioned between said topsheet 30 and said backsheet 40. The absorbent core 50 comprises an absorbent layer 56 and first and second tissue layers 57 and 58, respectively, which envelope the absorbent layer 56. Also, the absorbent core 50 has core side edges 53 and core waist edges 54.

Joined to the chassis means 15 are the integral belt segments 72. The integral belt segments 72 are elongated members or combinations of members which are generally conformable and non-irritating to the wearer's skin and which act in concert with each other to hold or suspend the garment about the wearer's lower torso. As used herein, the term "joined" includes any means for affixing the integral belt segments 72 to the chassis means 15, and includes embodiments wherein the integral belt segments 72 are separate members constructed from the same or different material as an element of the chassis means 15 and directly or indirectly secured to the chassis means 15 (i.e., integral) and embodiments wherein the integral belt segments 72 are constructed from the same material as an element of the chassis means 15 in such a way that the integral belt segments 72 are continuous and undivided elements of the chassis means 15 (i.e., unitary). In the preferred embodiment shown in FIG. 1, the integral belt segments 72 are a laminate of topsheet 30 and backsheet 40 material which have been directly secured to the back surface 31 of the backsheet 40.

The chassis means 15 has a liquid receiving top surface 32 which is generally defined by the topsheet 30 and a back surface 31 which is generally defined by the backsheet 40. Preferably, the topsheet 30 and the backsheet 40 have length and width dimensions generally larger than the absorbent core 50, so that they extend beyond the core side edges 53 and the core waist edges 54 of the absorbent core 50 where they are associated together in a suitable manner. As used herein, the term "associated" encompasses configurations whereby the topsheet 30 is directly joined to the backsheet 40 by affixing the topsheet 30 directly to the backsheet 40 and configurations whereby the topsheet 30 is indirectly joined to the backsheet 40 by affixing the topsheet 30 to intermediate members which in turn are affixed to the backsheet 40. In the preferred embodiment shown in FIG. 1, the extension of the topsheet 30 and/or the backsheet 40 beyond the core side edges 53 of the absorbent core 50 forms the chassis side edges 27. The extension of the topsheet 30 and/or the backsheet 40 beyond the core waist edges 54 of the absorbent core 50 forms the chassis front and chassis back end edges 28 and 29, respectively. The chassis front and chassis back end edges 28 and 29 and the chassis side edges 27 comprise the periphery 26 of the chassis means 15.

Examining some of the elements of the diaper 20 in more detail, the topsheet 30 is positioned adjacent the body surface 51 of the absorbent core 50 and overlays a major portion of the absorbent core 50, so that when exudates are discharged onto the topsheet 30 they penetrate through the topsheet 30 where they are absorbed by the absorbent core 50. The topsheet 30 is compliant, soft feeling, and non-irritating to the wearer'skin. Further, the topsheet 30 is liquid pervious, permitting liquids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g., polyester of polypropylene fibers) or from a combination of natural and synthetic fibers. Preferably, it is made of hydrophobic material to isolate the wearer's skin from liquids in the absorbent core 50. A particularly preferred topsheet 30 comprises staple length polypropylene fibers having a denier of about 1.5, such as Hercules Type 151 polypropylene marketed by Hercules, Inc. of Wilmington, Del. As used herein, the term "staple length fibers" refers to those fibers having a length of at least about 15.9 millimeters (0.625 inches).

There are a number of manufacturing techniques which may be used to manufacture the topsheet 30. For example, the topsheet 30 may be woven, non-woven, spunbonded, carded, or the like. A preferred topsheet 30 is carded and thermally bonded by means well known to those skilled in the fabrics art. Preferably, the topsheet 30 has a weight from about 18 to about 25 grams per square meter, a minimum dry tensile strength of at least about 400 grams per centimeter in the machine direction and a wet tensile strength of at least about 38 grams per centimeter in the cross-machine direction.

The absorbent core 50 may be any means which is generally compressible, conformable, non-irritating to the wearer's skin, and capable of absorbing and containing liquids and certain body exudates. A preferred absorbent core 50 has a body surface 51 and a garment surface 52 and comprises an absorbent layer 56 and first and second tissue layers 57 and 58, respectively. The first and second tissue layers 57 and 58 overlay the major surfaces of the absorbent layer 56 to form the body surface 51 and the garment surface 52 of the absorbent core 50.

The absorbent layer 56 may be manufactured in a wide variety of sizes and shapes (e.g., rectangular, hourglass, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent layer 56 should, however, be compatible with the design exudate loading for the intended use of the diaper 20. Further, the size and absorbent capacity of the absorbent layer 56 may be varied to accommodate wearers ranging from infants to adults.

A preferred embodiment of the diaper 20 has an hourglass shaped absorbent layer 56 and is intended to be worn by adults. The absorbent layer 56 is preferably a batt of airfelt about 16 centimeters (6.4 inches) wide (lateral dimension along the core waist edges 54), about 45 centimeters (18.0 inches) long (longitudinal dimension) and about 11 centimeters (4.4 inches) across (lateral dimension) the narrowest part of the crotch region 25. The airfelt use in the absorbent layer 56 has a generally uniform caliper of about 1.0 centimeter (0.40 inch), an absorbent capacity of from about 8 grams to about 16 grams of water per gram of absorbent material, and a weight from about 0.03 grams per cubic centimeter to about 0.07 grams per cubic centimeter. It should be understood, however, that the size, shape, configuration, and total absorbent capacity of the absorbent layer 56 may be varied to accommodate wearers ranging from infants through adults. Therefore, the dimensions, shape, and configuration of the absorbent layer 56 may be varied (e.g., the absorbent layer may have a varying caliper, or a hydrophyllic gradient or may contain absorbent gelling materials).

The first and second tissue layers 57 and 58 improve the tensile strength of the absorbent core 50 and reduce the tendency of the absorbent layer 56 to split, lump or ball when wetted. The first and second tissue layers 57 and 58 also help to improve lateral wicking of the absorbed exudates, thereby providing a more even distribution of the exudates throughout the absorbent layer 56. While a number of materials and manufacturing techniques may be used to manufacture the first and second tissue layers 57 and 58, satisfactory results have been obtained with sheets of tissue paper having a basis weight of about 16 grams per square meter (ten pounds per 3,000 square feet) and having an air permeability of about 30.5 cubic meters per minute per square meter (100 cubic feet per minute per square foot) at a pressure differential of about 12.8 millimeters of water (0.5 inch). While the first and second tissue layers 57 and 58 are preferably coterminous with the absorbent layer 56, they may have different dimensions, a different configuration, or they may be omitted entirely.

The backsheet 40 is positioned adjacent the garment surface 52 of the absorbent core 50 and is preferably attached thereto by attachment means (not shown) such as those well known in the art. For example, the backsheet 40 may be secured to the absorbent core 50 by a uniform continuous layer of adhesive, a patterned layer of adhesive, or an array of separate lines or spots of adhesive. Adhesives which have been found to be satisfactory are manufactured by Eastman Chemical Products Company of Kingsport, Tenn., and marketed under the tradename Eastobond A-3 and by Century Adhesives, Inc. of Columbus, Ohio and marketed under the tradename Century 5227.

The backsheet 40 is impervious to liquids and is preferably manufactured from a thin plastic film, although other flexible liquid impervious materials may also be used. The backsheet 40 prevents the exudates absorbed and contained in the absorbent core 50 from wetting articles which contact the diaper 20, such as bedsheets and undergarments. Preferably, the backsheet 40 is a polyethylene film having a thickness of from about 0.012 millimeters (0.5 mil) to about 0.051 centimeters (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as film No. 8020. The backsheet 40 is preferably embossed and/or matte finished to provide a more clothlike appearance. Further, the backsheet 40 may permit vapors to escape from the absorbent core 50 while still preventing exudates from passing through the backsheet 40.

The size of the backsheet 40 and/or the topsheet 30 are dictated by the size of the absorbent core 50 and the exact diaper design selected. In a preferred embodiment, the backsheet 40 and the topsheet 30 have a rectangular shape and extend beyond the core size edges 53 of the absorbent core 50 a distance of from about 6.25 centimeters (2.5 inches) to about 8.75 centimeters (3.5 inches), and extend beyond the core waist edges 54 of the absorbent core 50 a distance of from about 7.5 centimeters (3.0 inches) to about 20 centimeters (8.0 inches) where they are joined directly to each other in the chassis side edges 27 and the chassis front and back end edges 28 and 29, respectively, by attachment means (not shown) as are well known in the art. The attachment means may be, for example, a uniform continuous layer of adhesive, a patterned layer of adhesive, or an array of separate lines or spots of adhesive.

The integral belt segments 72 are joined to the chassis means 15 at their fixed points 60. A fixed point 60 is a point on an integral belt segment 72 at which an integral belt segment 72 is permanently joined to the chassis means 15. The integral belt segments 72 can be joined to the chassis means 15 in a number of ways and at a number of points on the chassis means 15 and the fixed points 60 may be at a number of points on the integral belt segments 72. Each integral belt segment 72 has a distal portion 75 which is free from the chassis means 15 and which extends away from the fixed point 60. In use, a part of the distal portion 75 is associated with the chassis means 15 either directly or indirectly, to hold or suspend the diaper 20 about the lower torso of the wearer. The integral belt segments 72 have a distal point 76 which is the most distal point of the distal portion 75, measured from the fixed point 60.

Figure 2:
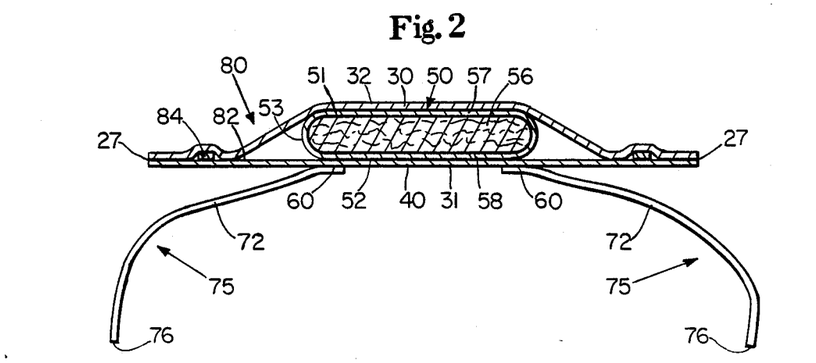
FIG. 2 is a fragmentary sectional view taken along section line 2—2 of FIG. 1.
Figure 3:
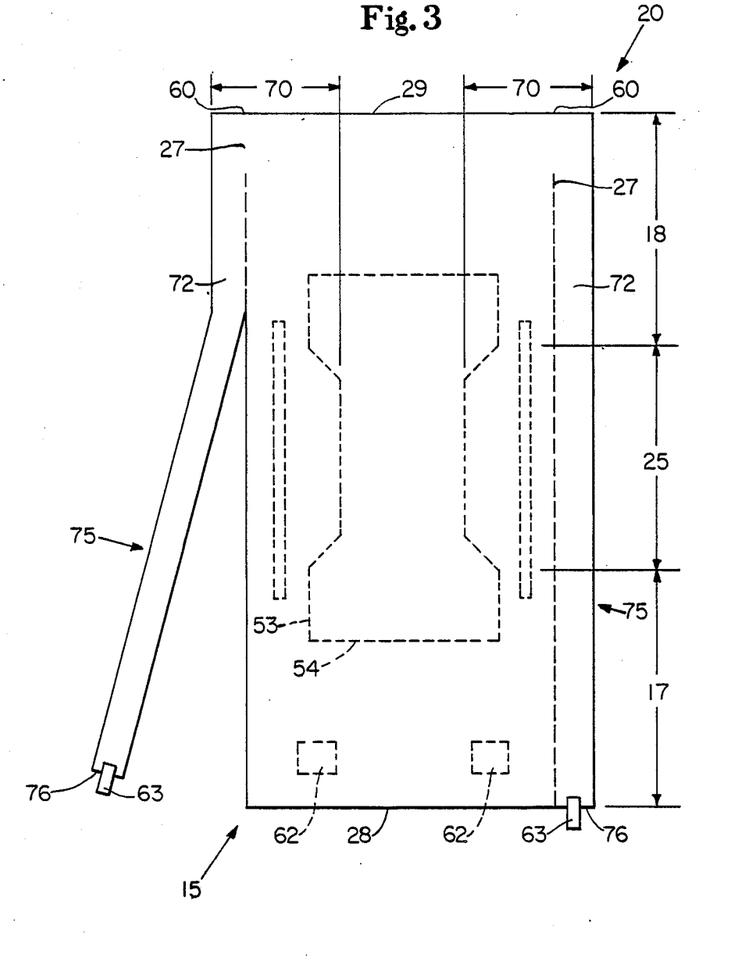
FIG. 3 is a plan view of an alternatively preferred disposable diaper embodiment of the present invention with the portion of the diaper which contacts the wearer facing the viewer and with a portion of one integral belt segment having been pulled away from the chassis means.

FIG. 3 shows a preferred embodiment of present invention in which the integral belt segments 72 are formed from the chassis means 15, itself, in the side margins 70. A side margin 70 comprises those parts of the chassis means 15 between a chassis side edge 27 and an imaginary line drawn parallel to the longitudinal centerline 33 and passing through a point along the core side edge 53 which corresponds to the narrowest lateral width of the absorbent core 50. In the preferred embodiments shown in FIGS. 1 through 6, the side margins 70 primarily comprise a laminate of the topsheet 30 and the backsheet 40. Alternatively, the side margins 70 might consist only of the topsheet 30, or only the backsheet 40, or one other member or material, or the side margins 70 might comprise a laminate of any number of members or materials.

In a preferred embodiment, the integral belt segments 72 are formed by making a longitudinal cut in the side margins 70, in and through the chassis means 15. In the more preferred embodiment shown in FIG. 3, the integral belt segments 72 are formed by making a longitudinal cut in the side margins 70, in and through the topsheet 30 and the backsheet 40. As used herein, the term "cut" is intended to include complete and uninterrupted cuts so that the integral belt segments 72 are free from the chassis means 15 along the length of the cut, and also perforations, which are a series of cut-outs and uncut bonds which are easily broken but which allow the integral belt segments 72 to remain temporarily attached to the chassis means 15 for easier packing and handling until needed for use. Thus, the chassis means 15, which was originally of a certain width (lateral dimension), is, after the cuts, now decreased on each side by a dimension that corresponds to the width of each integral belt segment 72. Further, the chassis side edges 27 now correspond to the cuts and extend longitudinally beyond an end of the cuts to the chassis back end edge 29. In the preferred embodiment shown in FIG. 3, the cut is of the perforation type and is begun about 5 centimeters (2.5 inches) from the back end edge 29 of the periphery 26 and ends at the front end edge 28. Thus, in this preferred embodiment, the integral belt segments 72 are unitary with the chassis means 15 in that they are continuous and undivided elements of the chassis means 15, and they are joined to the chassis means 15 adjacent to the chassis side edges 27. In this preferred embodiment, the integral belt segments 72 are joined to the chassis means 15 at their fixed points 60 in the back region 18 along the back end edge 29.

Figure 4:
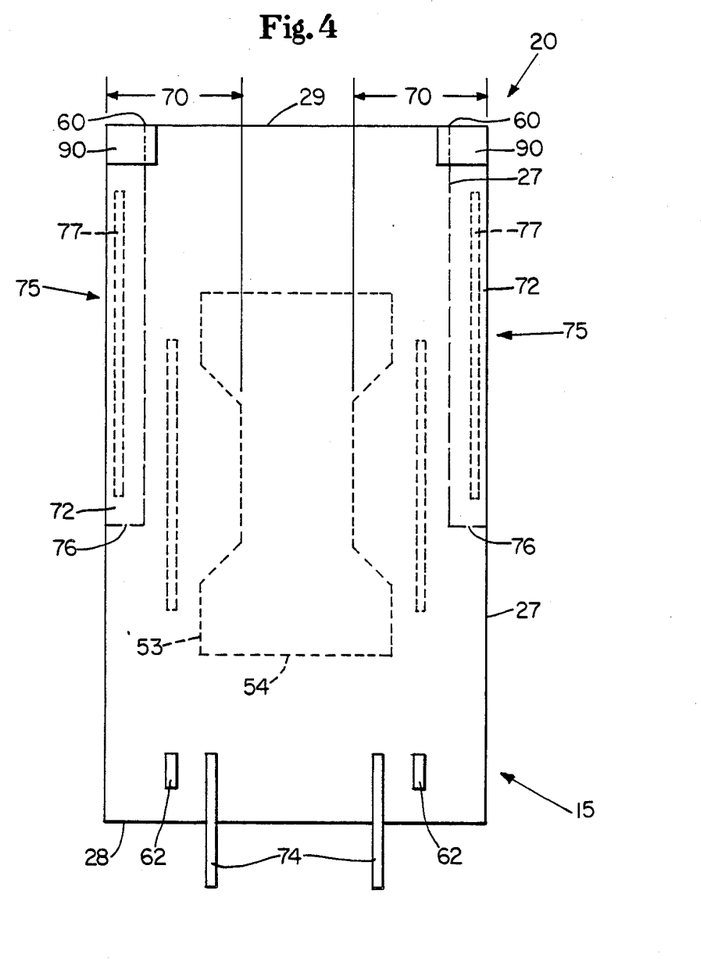
FIG. 4 is a plan view of another alternatively preferred disposable diaper embodiment of the present invention with the portion of the diaper which contacts the wearer facing away from the viewer.
Figure 5:
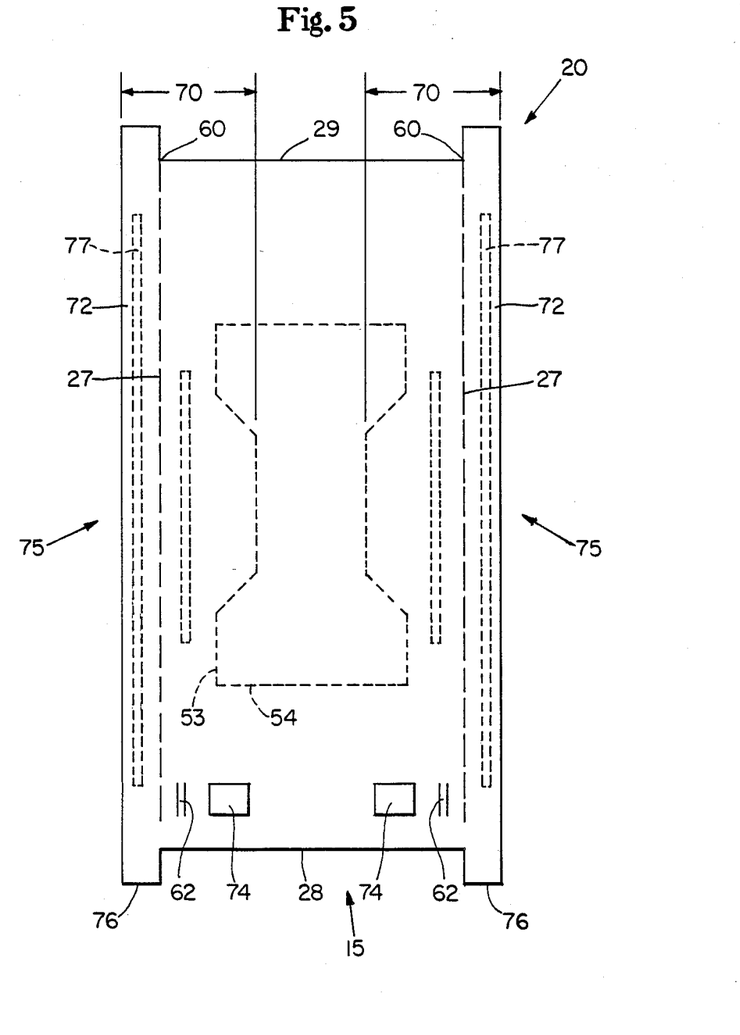
FIG. 5 is a plan view of another alternatively preferred disposable diaper embodiment of the present invention with the portion of the diaper which contacts the wearer facing away from the viewer.

Receiving means 62 are joined to the chassis means 15 for use in association with the integral belt segments 72. As used herein, the term "joined" includes any means for affixing the receiving means 62 to the chassis means 15, and includes embodiments wherein the receiving means 62 are separate members constructed from the same or from a different material as an element of the chassis means 15 and directly or indirectly secured to the chassis means 15 (i.e., integral) and embodiments wherein the receiving means 62 are constructed from the same material as an element of the chassis means 15 in such a way that the receiving means 62 are continuous and undivided elements of the chassis means 15 (i.e., unitary). The receiving means 62 are provided to receive and hold the integral belt segments 72 and in association with the integral belt segments 72 and the chassis means 15 are intended to hold or suspend the chassis means 15 about the lower torso of the wearer. In the preferred embodiment shown in FIG. 1, the receiving means 62 are joined to the back surface 31 of the chassis means 15 near the front end edge 28. In this preferred embodiment, the receiving means 62 comprises a pair of double-faced adhesive tapes. Other receiving means 62 are available. For instance, FIGS. 4 and 5, which are plan views of alternative embodiments of the present invention with the portions of the diapers 20 which contact the wearer facing away from the viewer, show an alternatively preferred receiving means 62 which utilizes a pair of belt loops 62 through which the single integral belt segments 72 can be brought and then tied together or associated with a second receiving means 74, such as the foldover adhesive tape shown in FIG. 4. The belt loops 62 can be separate members which are attached to the back surface 31 of the chassis means 15 as shown in FIG. 4. Alternatively, the belt loops 62 can be formed by cutting slits in the backsheet 40 as shown in FIG. 5, through which the single integral belt segments 72 can be brought. Other alternative receiving means 62 are mechanical type fasteners such as velcro, snaps, or hooks which interact with the integral belt segments 72.

Instead of, or in conjunction with, receiving means 62, attachment means 63 may be joined to the integral belt segments 72. The attachment means 63 are joined to the integral belt segments 72 and are used to attach the integral belt segments 72 to the chassis means 15. The attachment means 63, in association with the integral belt segments 72, the chassis means 15 and/or the receiving means 62, are intended to hold or suspend the chassis means 15 about the lower torso of the wearer. A preferred attachment means 63, as shown in FIG. 3, is a tape tab fastener, such as the fastening tape disclosed in U.S. Pat. No. 3,848,594 entitled "Tape Fastening System For Disposable Diaper", which issued to K. B. Buell on Nov. 19, 1974, and which patent is incorporated herein by reference. In this preferred embodiment, the tape tab fasteners are joined to the integral belt segments 72 near the distal points 76. In use, the tape tab fasteners are brought in contact with and joined to the back surface 31 of the backsheet 40. Alternatively, the attachment means 63 may be a double-faced adhesive tape or a coating of adhesive applied to the integral belt segments 72.

FIG. 2 is a fragmentary sectional view taken along line 2—2 of FIG. 1 and depicts a preferred diaper construction in the crotch region 25 of the diaper 20. The absorbent core 50 comprises the absorbent layer 56 that is shown as being completely enveloped by the first and second tissue layers 57 and 58. The absorbent core 50 is disposed between the topsheet 30 and the backsheet 40. The backsheet 40 extends beyond the core side edges 53 of the absorbent core 50 about 8.75 centimeters (3.5 inches) to the chassis side edges 27 of the periphery 26. The topsheet 30 covers the body surface 51 of the absorbent core 50 and extends beyond the core side edges 53 of the absorbent core 50 inwardly and preferably adjacent to the chassis side edges 27 of the periphery 26 where it is preferably associated with the backsheet 40.

In a particularly preferred embodiment of the present invention, the diaper 20 has a pair of side flaps 82, one or more side flap elastic members 84 associated with each of said side flaps 82, and a pair of gasketing cuffs 80. The side flaps 82 comprise those portions of the diaper 20 between the core side edges 53 and the chassis side edges 27. The side flap elastic members 84 are operatively associated with the side flaps 82 so that they effectively contract or gather the side flaps 82 to provide gasketing cuffs 80 about the legs of the wearer. While the topsheet 30, the absorbent core 50, the backsheet 40, the side flaps 82, the side flap elastic members 84, and the gasketing cuffs 80 may be assembled in a variety of well known configurations, a preferred diaper configuration is described generally in U.S. Pat. No. 3,860,003 entitled "Contractable Side Portions For Disposable Diaper", which issued to K. B. Buell on Jan. 14, 1975, and which patent is incorporated herein by reference. In addition, a method and apparatus suitable for manufacturing a disposable diaper having elastically contractible gasketing cuffs are described in U.S. Pat. No. 4,081,301 entitled "Method and Apparatus for Continuously Attaching Discrete, Stretched Elastic Strands to Predetermined Isolated Portions of Disposable Absorbent Products", which issued to K. B. Buell on March 28, 1979, and which patent is incorporated herein by reference.

The diaper 20 can also be divided into regions. As shown in FIG. 3, the diaper 20 has front and back waist regions 17 and 18, respectively, each extending inwardly from the chassis front and chassis back end edges 28 and 29, respectively, toward the lateral centerline 34 of the diaper 20 to points which are located inwardly from the core waist edges 54 a distance from about ¼ to about ⅓ the length of the absorbent core 50. The waist regions comprise those portions of the diaper 20 which, when worn, encircle the waist of the wearer. The diaper 20 also has a crotch region 25 which is that portion of the diaper 20 between the waist regions 17 and 18, and comprises that portion of the diaper 20 which, when worn, is positioned between the legs of the wearer and covers the lower torso of the wearer.

Figure 6:
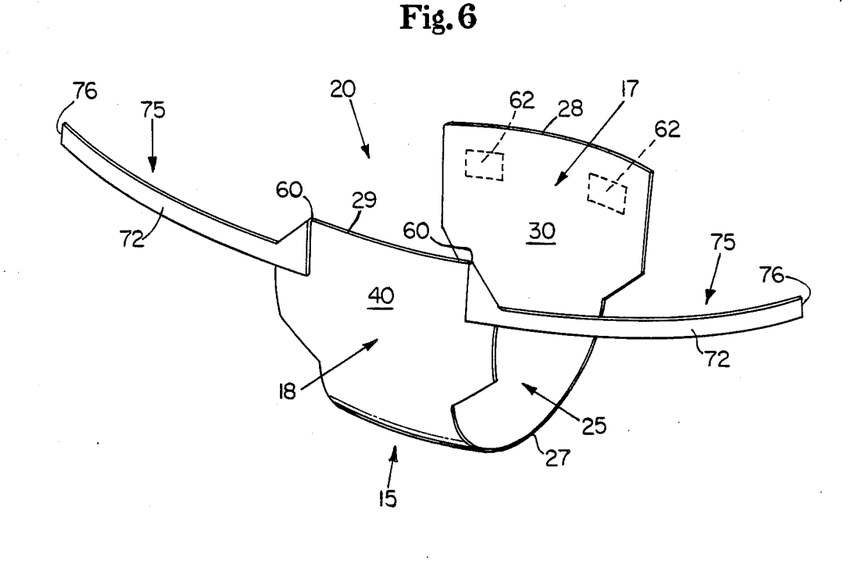
FIG. 6 is a perspective view of the disposable diaper as it would appear when ready for use.

FIG. 3 shows a preferred embodiment of the present invention in which the topsheet 30 and backsheet 40 have been perforated in the side margins 70 to form the integral belt segments 72. In use, the perforations can be broken with a finger causing the integral belt segments 72 to become detached from the chassis means 15 along the length of the cut. FIG. 6 is a view of the disposable diaper embodiment shown in FIG. 3 as it would appear when ready for use. After the perforations are broken, the diaper 20 is positioned between the wearer's legs so that the crotch region 25 covers the lower torso, and the waist regions 17 and 18 are positioned adjacent to the waist areas of the wearer so that the front waist region 17 covers the front waist and the back waist region 18 covers the back waist. The integral belt segments 72 are then brought across the wearer's hips as snugly or loosely as desired and associated with the receiving means 62 on the back surface 31 of the backsheet 40 in the front waist region 17 of the diaper 20.

As would be obvious to a person of ordinary skill in the art, the diaper 20 may take the form of a number of alternative embodiments. FIG. 4 shows an alternatively preferred embodiment of a disposable diaper 20 in which the integral belt segments 72 are formed in the side margins 70. In this alternatively preferred embodiment, the diaper material in each side margin 70 is longitudinally cut from the back end edge 29 to a point between the front and back end edges 28 and 29 where a lateral cut is made outwardly to the chassis side edge 27.

A reinforcing member 90 (i.e., a poly tape or the like) is then applied over the end of the cut along the back end edge 29 to form the fixed point 60 along the back end edge 29 and thereby prevent the integral belt segment 72 from being completely detachable from the chassis means 15. In this alternative embodiment, the chassis means 15, which originally had the shape of a large rectangle, is now decreased in width along a portion of its length equal to the length of the integral belt segments 72 an amount equal to the widths of the integral belt segments 72.

Alternatively, the integral belt segments 72 can be of varying length, for instance, one integral belt segment 72 might be only about one-half as long as said garment while the other integral belt segment 72 might be about one and one-half times as long as said garment.

Alternatively, the fixed and distal points 60 and 76, respectively, of the integral belt segments 72 can be located between or beyond the front and back end edges 28 and 29, respectively, as shown in FIGS. 4 and 5, respectively.

Also, alternatively, the integral belt segments 72 may be elastically contractible. A preferred method for making the integral belt segments 72 elastically contractible is to operatively associate them with one or more integral belt segment elastic members 77, as shown in FIGS. 4 and 5 so that they effectively contract or gather the integral belt segments 72 about the waist of the wearer to provide a snug fit.

Also, alternatively, the integral belt segments 72 can be completely separate members from the chassis means 15 which have been sewn, glued, or joined by any other means to the chassis means 15.

While particular embodiments of the present invention have been illustrated and described, it would be obvious to those skilled in the art that various other changes and modifications can be made without departing from the spirit and scope of the invention.

What is claimed is:

1. An integral disposable absorbent garment, comprising:
    a chassis means for absorbing and containing body exudates, said chassis means having longitudinally extending chassis side margins, laterally extending chassis end edges and chassis side edges;
    a waist belt attachment system, comprising:
    an integral belt segment cut from each said chassis means side margins and of a length at least equal to the length of said chassis means side margin, each of said integral belt segments having a fixed point and a distal point, said fixed point of each of said integral belt segments being joined to said chassis means and extending longitudinally outboard of one said chassis end edge; and
    a receiving means joined to said chassis means for receiving and holding said integral belt segments.

2. The integral disposable absorbent garment as claimed in claim 1, wherein said chassis means comprises:
    a liquid permeable topsheet;
    a liquid impermeable backsheet associated with said topsheet; and
    an absorbent core positioned between said topsheet and said backsheet, said absorbent core having core side edges and core waist edges.

3. The integral disposable absorbent garment as claimed in claim 2, wherein said fixed points of said integral belt segments are joined to said chassis means adjacent to said chassis side edges.

4. The integral disposable absorbent garment as claimed in claim 3, wherein said integral belt segments are elastically contractible.

5. The integral disposable absorbent garment as claimed in claim 3, wherein said integral belt segments have a length of at least about one-half the longitudinal length of said garment.

6. The integral disposable absorbent garment as claimed in claim 5, wherein said chassis means further comprises a back waist region, wherein said fixed points of said integral belt segments are located within said back waist region of said garment.

7. The integral disposable absorbent garment as claimed in claim 6, wherein said chassis means further comprises front and back end edges, and wherein said distal points of said integral belt segments are located between said front and said back end edges of said garment.

8. The integral disposable absorbent garment as claimed in claim 3, further comprising a back surface, wherein said receiving means is joined to said back surface.

9. The integral disposable absorbent garment as claimed in claim 8, wherein said receiving means is an adhesive tape.

10. The integral disposable absorbent garment as claimed in claim 8, wherein said receiving means is a belt loop.

11. The integral disposable absorbent garment as claimed in claim 8, wherein said receiving means is a mechanical fastener.

* * * * *

UNITED STATES PATENT AND TRADEMARK OFFICE
CERTIFICATE OF CORRECTION

PATENT NO. : 4,909,802

DATED : March 20, 1990

INVENTOR(S) : Nicholas A. Ahr and William G. Pierce

It is certified that error appears in the above-identified patent and that said Letters Patent is hereby corrected as shown below:

Column 1, line 57, reads "a" (2nd occur) should read --an--.

Column 4, line 50, reads "of" should read --or--.

Column 7, line 7, after "of" insert --the--.

Claims 2-11, "claim" should be --Claim--.

Signed and Sealed this

Seventeenth Day of December, 1991

Attest:

HARRY F. MANBECK, JR.

*Attesting Officer*  *Commissioner of Patents and Trademarks*